(12) United States Patent
Denimal et al.

(10) Patent No.: US 8,463,497 B2
(45) Date of Patent: Jun. 11, 2013

(54) METHOD FOR DETERMINING A WHEEL GRIP COEFFICIENT BY SIMULTANEOUS CLAMPING

(75) Inventors: Philippe Denimal, Chamalieres (FR); Jean-Marie Mus, Marsat (FR); Fabien Marlier, Clermont-Ferrand (FR); Lionel Fagot-Revurat, Barberier (FR)

(73) Assignees: Compagnie Generale des Etablissements Michelin, Clermont-Ferand (FR); Michelin Recherche et Technique S.A., Granges-Paccot (CH)

( * ) Notice: Subject to any disclaimer, the term of this patent is extended or adjusted under 35 U.S.C. 154(b) by 22 days.

(21) Appl. No.: 13/256,776

(22) PCT Filed: Mar. 18, 2010

(86) PCT No.: PCT/EP2010/053543
§ 371 (c)(1),
(2), (4) Date: Nov. 7, 2011

(87) PCT Pub. No.: WO2010/106137
PCT Pub. Date: Sep. 23, 2010

(65) Prior Publication Data
US 2012/0053786 A1 Mar. 1, 2012

(30) Foreign Application Priority Data

Mar. 19, 2009 (FR) ...................................... 09 51765

(51) Int. Cl.
*G06F 7/00* (2006.01)
(52) U.S. Cl.
USPC ........................................................... 701/36
(58) Field of Classification Search
USPC .................................... 701/36, 41, 80, 82, 90
See application file for complete search history.

(56) References Cited

U.S. PATENT DOCUMENTS

| | | | |
|---|---|---|---|
| 7,916,012 B2 | 3/2011 | Fargot-Revurat et al. | 340/447 |
| 2004/0019417 A1* | 1/2004 | Yasui et al. | 701/36 |
| 2005/0065699 A1 | 3/2005 | Bertrand | 701/80 |
| 2005/0234628 A1* | 10/2005 | Luders et al. | 701/80 |
| 2011/0040456 A1 | 2/2011 | Blondelet et al. | 701/49 |

FOREIGN PATENT DOCUMENTS

| | | |
|---|---|---|
| FR | 2 916 412 A1 | 11/2008 |
| WO | WO 00/75618 A1 | 12/2000 |
| WO | WO 03/066400 A1 | 8/2003 |

\* cited by examiner

*Primary Examiner* — Kim T Nguyen
(74) *Attorney, Agent, or Firm* — Fitzpatrick, Cella, Harper & Scinto

(57) ABSTRACT

A method for determining a characteristic quantity representative of grip conditions of a vehicle wheel running on a ground surface involves imposing a given simultaneous steering angle variation on two wheels mounted on the same axle of the vehicle, the steering angle variation being of the same amplitude for the two wheels but in opposite directions, and measuring the characteristic quantity for at least one of the two wheels.

21 Claims, 3 Drawing Sheets

METHOD FOR DETERMINING A WHEEL GRIP COEFFICIENT BY SIMULTANEOUS CLAMPING

FIELD OF THE INVENTION

The present invention relates to a method of determining a quantity characteristic of the grip conditions of a wheel of a vehicle running on a given ground.

TECHNOLOGICAL BACKGROUND

It is known that the grip conditions of a tyre running on a given ground, and especially its maximum grip coefficient, vary very greatly depending on the running conditions. Among the main factors are the type of road on which the wheel is running, the weather conditions and the temperature.

It is particularly advantageous to know in real time the grip conditions and especially the maximum grip coefficient of the running wheel in order to determine whether or not it is close to losing its grip on the ground.

This information relating to the grip of the wheel may be transmitted to the driver of the vehicle with which the wheel is fitted, so that he can adapt his driving accordingly, or to an electronic device for monitoring the road holding of the vehicle.

It has been shown in the prior art, especially in WO 03/066400, that it is possible to determine the maximum grip coefficient of the tyre of a wheel from measurements of the three components of the forces applied on the tyre, namely the self-alignment torque, the tyre inflation pressure and the tyre camber.

In particular, the above document specifies that it is possible to determine the maximum grip coefficient when there is a region of slip in the contact area between the running tyre and the ground. As soon as this region of slip occurs, for example for the same transverse force, the self-alignment torque is a monotonic function of the maximum grip coefficient.

This method of determining the maximum grip coefficient is limited as it can be implemented only under large acceleration or braking forces or on a bend.

Document FR 2 916 412 presents a motor-vehicle wheel assembly by means of a wheel holder associated with the vehicle by at least one pivot so that the plane of the wheel can make a substantially zero first toe angle and a non-zero second toe angle. The assembly comprises a binary actuator with a control device designed to shift the plane of the wheel under given running conditions.

DESCRIPTION OF THE INVENTION

In what follows, the term "wheel" is understood to mean an assembly consisting of a wheel (in the particular sense with a disc and a rim) and a tyre fitted onto the rim of the wheel.

By definition, each wheel of an axle of a vehicle makes an angle, called the steering angle, with a plane perpendicular to the ground and parallel to the direction of advance of the vehicle. When, on one and the same axle, the planes of the wheels of this axle converge so as to intersect towards the front of the vehicle, this is referred to as "toe setting". When, on one and the same axle, the planes of the wheels of this axle converge so as to intersect towards the rear of the vehicle, this is referred to as an "opening setting". The camber angle of a wheel is the angle that, in a plane perpendicular to the ground and containing the axis of the wheel, the plane of the wheel makes with the mid-plane of the vehicle. The counter-camber angle (or negative camber angle) refers to the case when the planes of the wheels on one and the same axle intersect above the ground.

The subject of the invention is a method of determining a characteristic quantity representative of the grip conditions of a wheel of a vehicle running on a given ground, comprising the following steps:

imposing on the two wheels of one and the same axle of the vehicle a given simultaneous steering angle variation, the steering angle variation being of the same amplitude for the two wheels but in opposite directions; and measuring the characteristic quantity for at least one of the two wheels.

According to this subject of the invention, a simultaneous steering angle setting is imposed on the two wheels of one and the same axle, preferably a simultaneous toe-in angle setting of these two wheels when the axle is a rear axle and a simultaneous toe-out angle setting of the two wheels when it is a front axle. This simultaneous toe angle (or opening angle) setting has the advantage that the transverse forces produced by the two wheels approximately compensate for each other and cancel each other out. The dynamic equilibrium of the vehicle is thus not disturbed. In particular, this simultaneous toe angle (or opening angle) setting is possible when the vehicle is running in a straight line, i.e., practically at any moment.

According to one particularly simple embodiment, a single simultaneous variation in the steering angles of the two wheels of one and the same axle may be imposed. Preferably, several simultaneous steering angle variations are imposed in succession on the two wheels of one and the same axle, the variations in the steering angles being of the same amplitude for the two wheels but in opposite directions.

This amounts to imposing or clamping a simultaneous toe angle (or opening angle) setting on the two wheels of one and the same rear (or front) axle with variable toe angle (opening angle) amplitudes.

Preferably, after having imposed a given simultaneous steering angle variation on the two wheels, the characteristic quantity is measured after a running distance of the vehicle greater than half the rolling perimeter of the wheels. This enables the forces transmitted by the wheels to be stabilized.

The measured characteristic quantity may be the self-alignment torque $M_Z$ of the wheel.

The measured characteristic quantity may also be the lateral force $F_Y$ of the wheel.

These two measurements, for a given steering angle, each give a first estimate of the grip conditions of the tyre in real time, which may be very useful.

Preferably, the measured characteristic quantity comprises the self-alignment torque $M_Z$ and the lateral force $F_Y$. By simultaneously measuring these two quantities it is possible to obtain an excellent estimate of the grip conditions of the tyre and especially the maximum grip coefficient by comparison between a chart and the measurements.

The fact of obtaining several measurement points greatly improves the precision of the estimates in real time.

For example, it is possible to obtain, by means of this method, a good estimate of the variation of, for example, the lateral force $F_Y$ with the steering angle β and especially the maximum value of this force and to use it as input data for the driving aid systems of the vehicle.

The order of magnitude of the imposed steering angles is preferably between 0.5 and 2 degrees and very preferably between 1 and 1.5 degrees. With these steering angle values, it is found that, for a very large majority of passenger vehicle tyres, there is a region of slip in the contact area, even under good grip conditions.

These imposed steering angle values also have the advantage of being practically undetectable by a passenger in the vehicle.

To improve the quality of the estimate, the inflation pressure of the tyre of the wheel may furthermore be measured.

It is possible, and preferable, to apply this simultaneous toe-in angle setting when the vehicle is running in a straight line.

The axle chosen is preferably a non-steerable non-powered axle. It is then desirable to check, before applying the simultaneous toe-in angle setting, that the axle is not subjected to a braking torque. The axial or longitudinal component $F_X$ of the forces is then practically zero and is not involved in estimating the characteristic quantity and $\mu_{max}$.

The axle may also be a powered axle. It is then desirable to check that the vehicle is not in an accelerating or braking phase.

BRIEF DESCRIPTION OF THE DRAWINGS

All the implementation details are given in the following description, supplemented by FIGS. 1 to 5 in which.

DETAILED DESCRIPTION OF EMBODIMENTS OF THE INVENTION

One subject of the invention is a method of determining a characteristic quantity representative of the grip conditions of a wheel of a vehicle running on a given ground, in which on the two wheels of one and the same axle a given steering angle variation is imposed, the steering angle variation being of the same amplitude for the two wheels but in opposite directions; and the characteristic quantity for at least one of the two wheels is measured.

It is preferable to apply a simultaneous toe angle (or opening angle) setting on the two wheels when the axle is a rear axle (or front axle). Applying the toe-in angle setting to both wheels of a rear axle of a vehicle improves the dynamic stability of the vehicle, while applying the toe-out angle setting to both wheels of a front axle of a vehicle results in similar consequences.

In what follows, the subjects of the invention will be illustrated in the case of a rear axle of a motor vehicle, with a simultaneous toe-in angle setting applied to the two wheels of this axle.

It is desirable to estimate or measure, in real time, the grip coefficient $\mu_{max}$ of a wheel running on a ground, or a characteristic quantity dependent on this coefficient.

It is known, for example from WO 03/066400 already mentioned, that $\mu_{max}$ depends especially on the following parameters:

the driving or braking force $F_X$ applied to the wheel;
the lateral thrust force or lateral force $F_Y$ applied to the wheel;
the load $F_Z$ supported by the wheel;
the self-alignment torque $M_Z$ or the moment about the vertical axis exerted on the tyre;
the camber of the wheel; and
the inflation pressure of the tyre of the wheel.

This is so when there is a region of slip in the area of contact between the tyre of the wheel and the ground on which it is running.

In fact, it is also common experience that a change in ground grip conditions, for example and going from a dry road to a wet road, considerably reduces the value of $\mu_{max}$ and in particular, for a given steering angle, considerably reduces the lateral force $F_Y$ and the self-alignment torque $M_Z$ as soon as this slip in the contact area appears.

Consequently, according to a first embodiment, the method according to the invention makes it possible to obtain a first estimate of a characteristic quantity associated with the grip conditions of a wheel based solely on the measured value of the lateral force or the self-alignment torque. This estimate is not very precise, but it does make it possible, for example, to warn the driver of degraded grip conditions or to modify the rules or control parameters governing the operation of stability assistance devices, such as ESP devices, or braking assistance devices, such as ABS devices.

Figure 1:
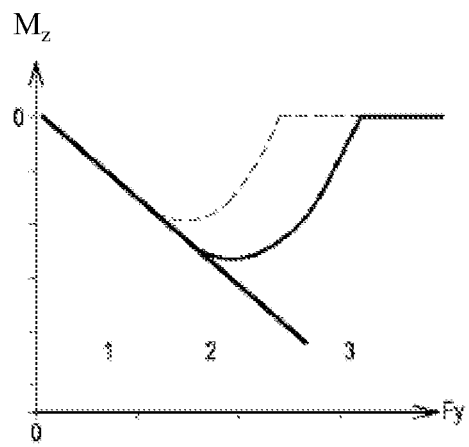
FIG. 1 illustrates the relationship between the self-alignment torque $M_Z$ and the lateral force $F_Y$ on an actual tyre as a function of the maximum grip coefficient $\mu_{max}$.

FIG. 1 illustrates the relationship between the self-alignment torque $M_Z$ and the lateral force $F_Y$ for two given grip coefficients $\mu_{max}$, when $F_X$ is zero and $F_Z$ is constant.

In this graph, three regions may be distinguished: region 1 corresponds to absence of slip of the area of contact with the tyre; region 2 corresponds to partial slip; and region 3 corresponds to total slip.

As may be seen, when the tyre is in region 1, i.e., when the tyre grips the ground perfectly, the self-alignment torque $M_Z$ is substantially proportional to the lateral thrust $F_Y$, the proportionality coefficient depending predominantly on the length of the contact area.

According to a preferred embodiment, the measured quantities characteristic of $\mu_{max}$ comprise at least the self-alignment torque $M_Z$ and the lateral force $F_Y$. It is then very easy to obtain a good estimate of the value of $\mu_{max}$ using a chart giving a series of self-alignment torque curves as a function of the lateral force for various $\mu_{max}$ values.

This approach is of good quality because the other parameters mentioned in document WO 03/066400 are either substantially constant (camber angle, inflation pressure, applied load) or are substantially zero ($F_X$).

A complementary measurement of the inflation pressure of the tyre or tyres of the wheels further improves the precision of the measurement.

One necessary condition is to impose a toe angle such that there is slip in the area of contact between the tyre and the ground. Trials carried out on a passenger vehicle tyre assembly have shown that when the toe angle is 0.5 degrees or less, this slip exists only under very degraded grip conditions. When a single toe angle is imposed, the imposed angle must therefore be greater than 0.5 degrees. However, when the imposed toe angle is around 2 degrees, the driver of the vehicle may start to be sensitive to this and the lateral thrust forces become very appreciable, which may result in tyres undergoing a certain wear. The imposed angles must therefore be preferably less than 2 degrees. A preferred range is between 1 and 1.5 degrees.

According to another embodiment of the method according to the invention, a simultaneous toe angle (or opening angle) setting is imposed in succession on the two wheels of one and the same axle when the axle is a rear axle (or a front axle) for several different amplitudes of the steering angle.

A complete or almost complete curve of the variation in the measured characteristic quantity as a function of the imposed steering angles can then be obtained. This allows the precision of the estimate to the maximum grip coefficient $\mu_{max}$ to be substantially improved.

According to another preferred embodiment, an increasing variation in the steering angle is imposed, preferably with a rate of variation of less than or equal to 0.1 degrees/metre traveled by the vehicle.

For an amplitude of two degrees, the distance traveled by the vehicle over the entire test is then equal to or greater than 20 metres.

More preferably, the rate of variation is between 0.05 and 0.1 degrees/metre traveled. The test then lasts between 20 and 40 metres.

It is then possible to measure, preferably continuously, the self-alignment torque for at least one of the two wheels and to determine, as characteristic quantity, the steering angle $\beta_c$ for which the self-alignment torque is a maximum.

This particular value of the self-alignment torque is important. Specifically, at this level of stressing of the wheel, there is slip in the area of contact between the tyre of the wheel and the roadway and, as noted earlier, for the same lateral force, the self-alignment torque is an increasing function of the maximum grip coefficient. The higher the critical steering angle $\beta_c$, the better the grip conditions between the wheel and the ground. This critical steering angle is thus a good indicator of the grip conditions in real time.

Preferably, both the self-alignment torque and the lateral force are measured and, after having determined the steering angle for which the self-alignment torque is a maximum, the lateral force $F_{yc}$ corresponding to this critical steering angle $\beta_c$ is determined as characteristic quantity.

This lateral force value $F_{yc}$ may be used as input data in driving assistance systems.

More preferably, after having determined the lateral force $F_{yc}$ corresponding to the critical steering angle $\beta_c$, the maximum lateral force $F_{ymax}$ of the wheel is estimated as characteristic quantity.

This quantity $F_{ymax}$ is an excellent indicator of the grip conditions of the wheel on the ground, and very useful input data for the driving assistance devices of the vehicle.

It is possible for $F_{ymax}$ to be simply estimated by the following formula:

$$F_{ymax}=F_{yc}\times K,$$

in which K is a characteristic coefficient of the wheel. It has been found experimentally that the value of this coefficient K is around 1.25 for very many tyres.

Knowing $F_{ymax}$, whenever the load $F_Z$ of the wheel is known, it is very easy to estimate the maximum grip coefficient $\mu_{max}$ by the formula:

$$\mu_{max}=F_{ymax}/F_Z.$$

The load on the wheel may be measured at the same time as the self-alignment torque and the lateral force, or by any other means well known to those skilled in the art.

This preferred embodiment, in which the imposed steering angles are progressively increased, has the advantage of requiring no prior knowledge about the wheels. Preferably, the test is stopped when the critical steering angle is determined, in such a way that the lateral force $F_y$ remains below 85% of the estimated maximum lateral force.

This limit has the advantage of maintaining good vehicle stability.

The methods, forming the subject matter of the invention, may be implemented with the device described below.

Figure 2:
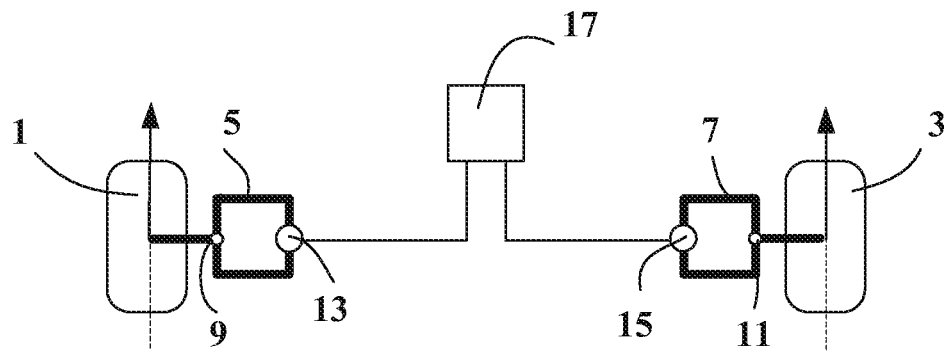
FIGS. 2 and 3 illustrate very schematically, in top view, the operation of the method according to one of the subjects of the invention in the case of a rear axle of a motor vehicle, the two wheels being at the usual toe angle close to zero (FIG. 2) and at a non-zero toe angle (FIG. 3)
Figure 3:
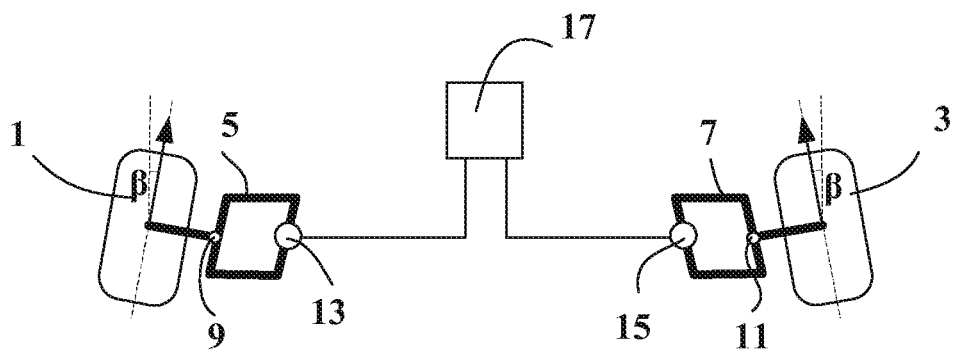

FIGS. 2 and 3 illustrate very schematically the operation of a device for implementing the method described above in the case of a motor-vehicle bearing rear axle. These figures are top views of the essential components of the device.

These figures show the left rear wheel 1 and the right rear wheel 3. Each of these wheels is mounted on a stub axle carrier system, 5 and 7 respectively. Each stub axle carrier system 5, 7 defines a pivot of vertical axis, 9 and 11 respectively, thereby enabling the steering angle of the wheel to be varied. Each stub axle carrier system also includes an actuator, 13 and 15 respectively, in order to apply the steering angle. The two actuators 13 and 15 are controlled by a common control device 17.

In FIG. 2, the two wheels 1 and 3 are in their usual position as recommended by the vehicle manufacturer. In FIG. 3, the two wheels are shown with a toe angle β of around 1 to 1.5 degrees. The arrows indicate the direction of travel of the vehicle. Each stub axle carrier system 5, 7 comprises means for measuring the steering lateral forces or thrusts and the self-alignment torque resulting from the steering angle setting of the wheels. The control device 17 comprises means for processing the signals, making it possible to estimate a quantity dependant on the maximum coefficient of friction of the wheel on the ground by comparison with, for example, charts and to transmit the resulting data to the driver or to the electronic devices of the vehicle.

Figure 4:
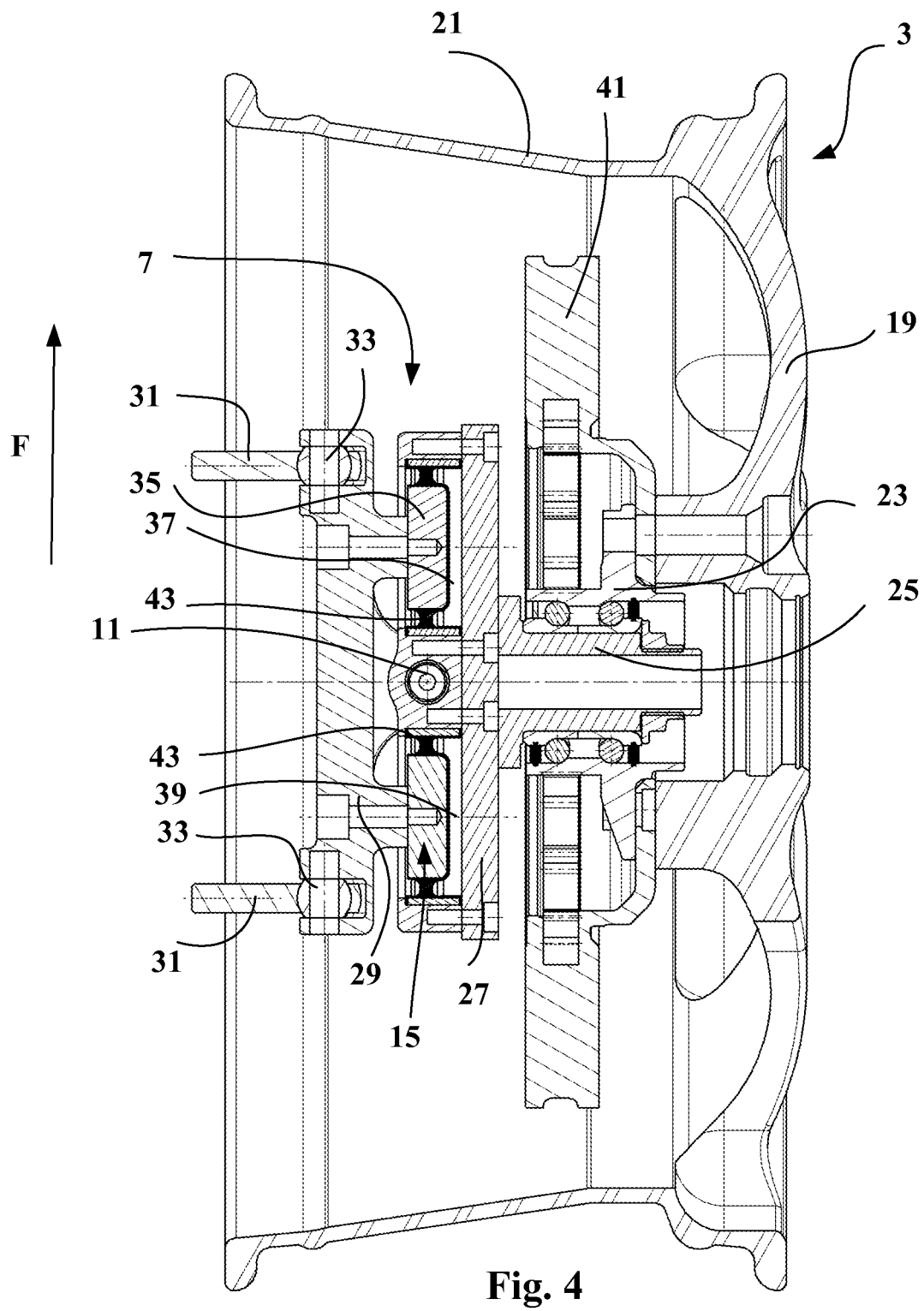
FIG. 4 shows, in horizontal cross section, one embodiment of a wheel assembly for implementing a method according to the invention.

FIG. 4 shows in horizontal cross section one embodiment of a wheel assembly according to one of the subjects of the invention.

The wheel 3 is in a right rear position of a vehicle. The arrow F indicates the direction of travel of the vehicle. This wheel comprises a tyre (not shown), a disc 19 and a rim 21.

The wheel 3 is rotationally mounted on a sensor bearing/wheel holder cassette 23 fastened onto the stub axle 25.

This sensor bearing/wheel holder cassette is provided with extensometry gauges for measuring the strains on the fixed race of the bearing, this race being subjected to the forces and moments that are developed upon contact between the wheel and the ground. An example of such a bearing cassette is the ASB3® force sensor from the company SNR Roulements [SNR Bearings].

The stub axle is linked to the vehicle via a stub axle carrier system 7 supporting a central pivot 11 enabling the plane of the wheel to be placed in two or more than two angular positions by pivoting the system 7 relative to the body of the vehicle.

The stub axle carrier system 7 comprises a stub axle holder 27 fitted with an actuator 15 and a plate 29 for linking to the body via the suspension arms 31. The suspension arms 31 are connected to the plate 29 via flexible joints or ball joints 33 having a substantially horizontal axis.

In the example shown, the actuator 15 comprises a hydroelastic cylinder 35 with two chambers 37 and 39 filled with an incompressible fluid under a variable pressure. The chambers are closed by resilient parts 43, for example made of a rubber material, which are capable of deforming under the influence of the respective pressures in the chambers 37 and 39 and thus imposing a variable steering angle on the wheel.

Depending on the method of controlling the hydroelastic cylinder, this actuator may be a binary or a non-binary actuator. In other words, it may have two or more than two setting positions.

Figure 5:
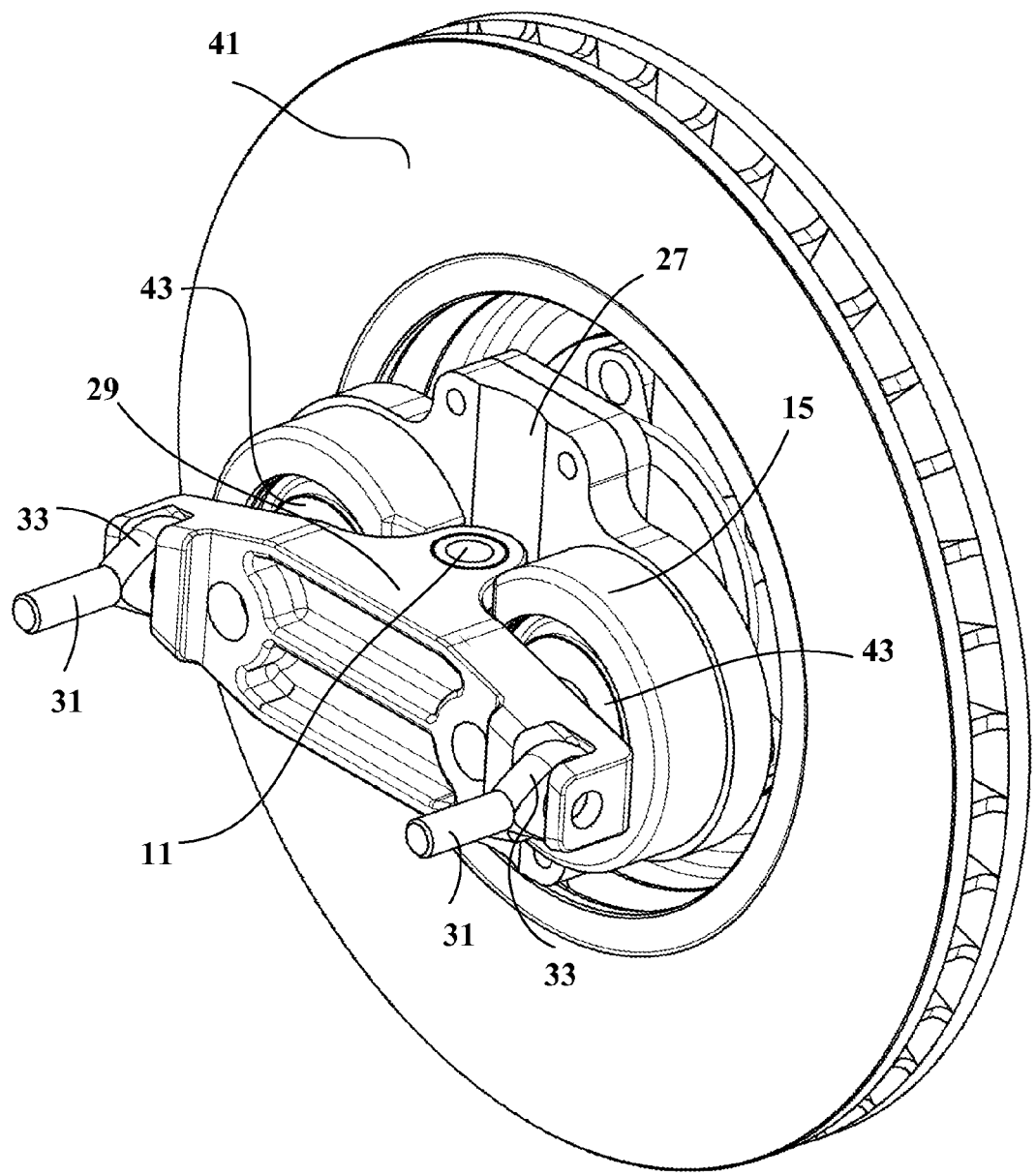
FIG. 5 shows a view, in partial perspective, seen from the vehicle body side, of the wheel assembly of FIG. 4.

FIG. 5 is a view, in partial perspective, on the body side, of the wheel assembly of FIG. 4. Shown in FIG. 5 are the ends of the suspension arms 31, the ball joints 33, the linkage plate 29 with the pivot 11, and the stub axle holder 27 with the actuator 15. Also shown is the brake disc 41 joined to the wheel holder.

The invention is not limited to the examples described and illustrated, and various modifications may be made thereto without departing from the scope thereof, as defined by the appended claims.

The invention claimed is:

1. A method of determining a characteristic quantity representative of a grip condition of a wheel of a vehicle running on a ground surface, the method comprising:
   utilizing an output of a control processor to simultaneously impose on two wheels of a same axle of the vehicle a given steering angle variation, the steering angle variation being of a same amplitude for the two wheels but in opposite directions; and
   measuring the characteristic quantity for at least one of the two wheels.

2. The method according to claim 1, wherein
   the two wheels of the same axle of the vehicle are two wheels of a rear axle of the vehicle, and
   a toe-in angle setting is imposed simultaneously on the two wheels of the rear axle of the vehicle.

3. The method according to claim 1, wherein
   the two wheels of the same axle of the vehicle are two wheels of a front axle of the vehicle, and
   a toe-out angle setting is imposed simultaneously on the two wheels of the front axle of the vehicle.

4. The method according to claim 1, wherein
   plural steering angle variations are imposed in succession on the two wheels of the same axle simultaneously, the steering angle variations being of a same amplitude for the two wheels but in opposite directions.

5. The method according to claim 4, wherein the plural steering angle variations imposed in succession increase monotonically, with a rate of variation being less than or equal to 0.1 degrees/meter traveled by the vehicle.

6. Method according to claim 5, wherein the measuring of the characteristic quantity includes:
   measuring a self-alignment torque for at least one of the two wheels; and
   determining, as the characteristic quantity, a steering angle ($\beta_c$) for which the self-alignment torque is a maximum.

7. Method according to claim 5, wherein the measuring of the characteristic quantity includes:
   measuring a self-alignment torque for at least one of the two wheels;
   determining a steering angle ($\beta_c$) for which the self-alignment torque is a maximum; and
   determining, as the characteristic quantity, a lateral force ($F_{yc}$) corresponding to the steering angle ($\beta_c$).

8. The method according to claim 5, wherein the measuring of the characteristic quantity includes:
   measuring a self-alignment torque for at least one of the two wheels;
   determining a steering angle ($\beta_c$) for which the self-alignment torque is a maximum;
   determining a lateral force ($F_{yc}$) corresponding to the steering angle ($\beta_c$); and
   estimating a maximum lateral force ($F_{ymax}$) of the at least one of the two wheels as the characteristic quantity.

9. The method according to claim 8, wherein the maximum lateral force ($F_{ymax}$) of the at least one of the two wheels is estimated by:

$$F_{ymax}=F_{yc}\times K,$$

in which K is a characteristic coefficient of the at least one of the two wheels.

10. The method according to claim 9, wherein, when a load ($F_Z$) on the at least one of the two wheels is known, the maximum lateral force ($F_{ymax}$) is used to estimate a maximum grip coefficient by:

$$\mu_{max}=F_{ymax}/F_Z.$$

11. The method according to claim 8, further comprising determining a maximum steering angle corresponding to a lateral force that is below 85% of the maximum lateral force ($F_{ymax}$).

12. The method according to claim 1, wherein, after the imposing of the given steering angle variation on the two wheels, the characteristic quantity is measured after a running distance of the vehicle greater than half a tire perimeter of a tyre of one of the two wheels.

13. The method according to claim 1, wherein the characteristic quantity is a self-alignment torque ($M_Z$) on a tyre of one of the two wheels.

14. The method according to claim 1, wherein the characteristic quantity is a lateral force ($F_Y$) on a tyre of one of the two wheels.

15. The method according to claim 1, wherein the characteristic quantity includes a self-alignment torque ($M_Z$) and a lateral force ($F_Y$).

16. The method according to claim 1, wherein the steering angle variation is between 0.5 and 2 degrees.

17. The method according to claim 1, wherein the steering angle variation is between 1 and 1.5 degrees.

18. The method according to claim 1, further comprising, after the characteristic quantity is measured, determining a grip coefficient of a tyre of one of the two wheels using a chart that associates the characteristic quantity with the grip coefficient.

19. The method according to claim 1, wherein the vehicle is running in a straight line.

20. The method according to claim 1, wherein, when the axle is a nonsteerable and non-powered axle, a check is made that the axle is not subjected to a braking torque before the steering angle variation is imposed on the two wheels.

21. The method according to claim 1, wherein, when the axle is a powered axle, a check is made that the vehicle is not in an accelerating phase or a braking phase before the steering angle variation is imposed on the two wheels.

* * * * *